United States Patent
Ninomiya et al.

(10) Patent No.: US 10,456,100 B2
(45) Date of Patent: Oct. 29, 2019

(54) X-RAY IMAGING DEVICE

(71) Applicant: Hitachi, Ltd., Tokyo (JP)

(72) Inventors: Atsushi Ninomiya, Tokyo (JP); Katsumi Usami, Tokyo (JP); Masaru Yokoyama, Tokyo (JP); Kazuyuki Yanase, Tokyo (JP); Kaoru Yamamoto, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 210 days.

(21) Appl. No.: 15/541,828

(22) PCT Filed: Mar. 17, 2016

(86) PCT No.: PCT/JP2016/058571
§ 371 (c)(1),
(2) Date: Jul. 6, 2017

(87) PCT Pub. No.: WO2016/152739
PCT Pub. Date: Sep. 29, 2016

(65) Prior Publication Data
US 2018/0000434 A1  Jan. 4, 2018

(30) Foreign Application Priority Data
Mar. 23, 2015 (JP) .................................. 2015-060072

(51) Int. Cl.
*A61B 6/00* (2006.01)
(52) U.S. Cl.
CPC .......... *A61B 6/4405* (2013.01); *A61B 6/4452* (2013.01); *A61B 6/4458* (2013.01); *A61B 6/462* (2013.01)

(58) Field of Classification Search
CPC ... A61B 6/4405; A61B 6/4452; A61B 6/4458; A61B 6/462
See application file for complete search history.

(56) References Cited

U.S. PATENT DOCUMENTS

| 5,265,149 A | 11/1993 | Varisco |
| 6,851,853 B2 | 2/2005 | Nakagawa et al. |

(Continued)

FOREIGN PATENT DOCUMENTS

| JP | 4-24917 A | 1/1992 |
| JP | 5-76406 U | 10/1993 |

(Continued)

OTHER PUBLICATIONS

International Preliminary Report on Patentability received in corresponding International Application No. PCT/JP2016/058571 dated Oct. 5, 2017.

(Continued)

*Primary Examiner* — Christine S. Kim
(74) *Attorney, Agent, or Firm* — Mattingly & Malur, PC

(57) ABSTRACT

Provided is an X-ray imaging device having a foldable arm unit for supporting an X-ray tube, and an operating unit for operating the X-ray tube, on a joint of arms constituting the arm unit. The operating unit is, for instance, a display unit serving also as the operating unit (display unit with a touch panel), and it is detachable from the joint of the arms. As another operating unit, a handle for operating the arm unit is provided. The handle for operating the arm unit can be provided with an operating switch for operating the X-ray tube. With this configuration, the X-ray imaging device being superior in operability and easy in checking the displayed information can be provided, at any height the X-ray tube is positioned.

15 Claims, 11 Drawing Sheets

(56) References Cited

U.S. PATENT DOCUMENTS

| | | | |
|---|---|---|---|
| 8,672,543 B2 | 3/2014 | Kralles et al. | |
| 9,693,437 B2* | 6/2017 | Simmons | G01N 23/04 |
| 10,136,866 B2* | 11/2018 | Onobori | A61B 6/4458 |
| 2003/0190014 A1 | 10/2003 | Nakagawa et al. | |
| 2011/0249805 A1 | 10/2011 | Kralles et al. | |
| 2014/0177797 A1* | 6/2014 | Ogura | A61B 6/4405 |
| | | | 378/62 |
| 2015/0069256 A1* | 3/2015 | Nakata | A61B 6/4405 |
| | | | 250/393 |
| 2015/0313560 A1* | 11/2015 | Omura | A61B 6/107 |
| | | | 378/62 |
| 2016/0319986 A1* | 11/2016 | Horndler | A61B 8/4405 |
| 2018/0135797 A1* | 5/2018 | Lee | F16M 11/10 |

FOREIGN PATENT DOCUMENTS

| | | |
|---|---|---|
| JP | 6-26805 U | 4/1994 |
| JP | 2003-290185 A | 10/2003 |
| JP | 2012-045421 A | 3/2012 |
| JP | 2013-523400 A | 6/2013 |
| JP | 2014-73321 A | 4/2014 |
| JP | 2014-110872 A | 6/2014 |
| JP | 2014-155620 A | 8/2014 |
| WO | 2014/192111 A1 | 12/2014 |

OTHER PUBLICATIONS

Japanese Office Action received in corresponding Japanese Application No. 2015-060072 dated Sep. 19, 2017.
International Search Report of PCT/JP2016/058571 dated Jun. 14, 2016.

* cited by examiner

X-RAY IMAGING DEVICE

TECHNICAL FIELD

The present invention relates to an X-ray imaging device provided with an X-ray tube, for taking an image of a subject placed between the X-ray tube and an X-ray detector which are disposed in a manner facing to each other. More particularly, the invention relates to the X-ray imaging device that is suitable for a mobile X-ray imaging device especially used in a visiting car.

BACKGROUND ART

A mobile X-ray imaging device has a structure mounting on a carriage, an X-ray tube supporter such as a strut and an arm for supporting an X-ray tube, and a main body provided with a driving mechanism of the X-ray tube and a power supply, configured to perform imaging after moved to a location such as a hospital room, a subject targeted for imaging being in there. Generally, the X-ray tube supporter is installed forward relative to the main body in the traveling direction of the device. Therefore, there is a problem that the forward view is apt to be obstructed while the device is moved, and accordingly, there has been suggested a mechanism for supporting the X-ray tube only by the arm, eliminating the strut (Patent Document 1).

The main body of the mobile X-ray imaging device is provided integrally with a console having a display part and an operating part, for displaying a UI required for operating the device and checking an image being taken at the site where the imaging is performed (e.g., Patent Document 2).

PRIOR ART DOCUMENT

Patent Document

Patent Document 1
DESCRIPTION of U.S. Pat. No. 5,265,149
Patent Document 2
Japanese Unexamined Patent Application Publication No. 2012-45421

DISCLOSURE OF THE INVENTION

Problems to be Solved by the Invention

Upon taking an image by the foregoing X-ray imaging device, an operator is required to conduct works such as positioning the X-ray tube unit at an appropriate spot with respect to the X-ray detector and the subject, and providing imaging conditions such as information of the subject, tube voltage, and tube current, so as to irradiate the subject with X-rays to perform imaging.

In the conventional X-ray imaging devices, for example, the operator proceeds with the works sequentially as the following; i.e., the console is started up, power is turned on, the device is moved by manipulating a handle for transporting, and when the device arrives at the site for imaging, the operator moves toward the X-ray tube supporter for setting the X-ray tube, and thereafter, the operator moves back to the place facing the operating part of the console so as to input the imaging conditions and to perform imaging. The operator has to move back and forth frequently between the point for manipulating the X-ray tube unit and the point facing the console, during the time from when the device is moved to the imaging site to when the imaging is performed.

In the case where the X-ray imaging device has a structure that supports the X-ray tube by a foldable-type arm, the X-ray tube becomes high when the arm is extended, and therefore, this may cause difficulties in manipulating the X-ray tube in some cases. Imaging conditions such as tube voltage and tube current, displayed on the display part of the console cannot be checked, concurrently with manipulating the strut or the arm. Even though there is a device having the X-ray tube unit on which a simple monitor is provided for displaying the imaging conditions, it is not easy to check the monitor screen, because the X-ray tube is at a high position.

An object of the present invention is to provide an X-ray imaging device that solves those problems of the conventional X-ray imaging devices, in particular, of the mobile X-ray imaging device, the X-ray imaging device being superior in operability and easy in checking the displayed information.

Means for Solving the Problems

An X-ray imaging device of the present invention is provided with a foldable arm unit as a means of supporting an X-ray tube, and an operating unit for operating the X-ray tube unit, is attached to a joint between arms constituting the arm unit, thereby solving the foregoing problems.

The operating unit may be a display unit which also serves as the operating unit (touch-panel display), and it is removable from the joint of the arms.

Further, the operating unit may be a handle for operating the arm unit. The handle for operating the arm unit may be provided with an operating switch for operating the X-ray tube.

Advantages of the Invention

The operating unit also serving as the display unit, enabling an input operation and displaying information necessary for imaging in addition to an image being taken, is provided at the position where manipulation of the arm unit is performed. Therefore, user's operability in the works required for the imaging can be drastically improved.

In addition, the operating unit/display unit is made detachable from the joint of arms, allowing the operator to perform any operations such as input works and imaging operations at any position. Furthermore, a person other than the operator, for example, a patient being the subject, is also allowed to see the taken image on the spot.

An operating handle is provided on the arm unit, and this allows the X-ray tube to move at a higher position without manipulating the X-ray tube itself. In addition, switches for operating the X-ray tube are provided on the handle, and this enables positioning of the X-ray tube, from a place remote from the X-ray tube.

BRIEF DESCRIPTION OF THE DRAWINGS

FIG. 7(a) is a plan view thereof, and FIG. 7(b) is a side view of the handle;

BEST MODE FOR CARRYING OUT THE INVENTION

An embodiment of the present invention will now be described, where an X-ray imaging device of the present invention has been applied to a mobile X-ray imaging device. The X-ray imaging device of the present embodiment is provided with an X-ray tube unit, a main body having a drive unit for driving the X-ray tube unit, and an arm unit fixing the X-ray tube unit to an end thereof, coupling the X-ray tube unit with the main body, wherein the arm unit comprises plural foldable arms, and an operating unit for manipulating the X-ray tube unit is provided on a joint between two arms. The main body is mounted on a carriage and this makes the device movable.

One example of the operating unit is a touch panel display (an operating/display unit), and it is detachable from and attachable to the joint of the arms. Another example of the operating unit is a handle for manipulating the arm. The X-ray imaging device of the present embodiment is further provided with a cover that covers the joint of the arms, and the display unit also serving as the operating unit is mounted on the cover, together with the handle fixed thereto. The arm unit comprises a first arm coupled to the main body, and a second arm having the X-ray tube unit fixed on the end thereof, wherein the first arm is coupled to the main body in a slidable manner as well as rotatable in opening and closing directions, the second arm is coupled to the first arm, in a manner rotatable in opening and closing directions and swiveling around an axis in a longitudinal direction of the first arm, and the handle is used for manipulating the rotation of the first arm, and the rotation and swiveling of the second arm.

In the X-ray imaging device of the present embodiment, the handle is provided with an operating switch (operating unit) for controlling the operation of the X-ray tube unit. The operation of the X-ray tube unit may include at least one of the operations such as rotation, swiveling, and swing motion.

Figure 1:
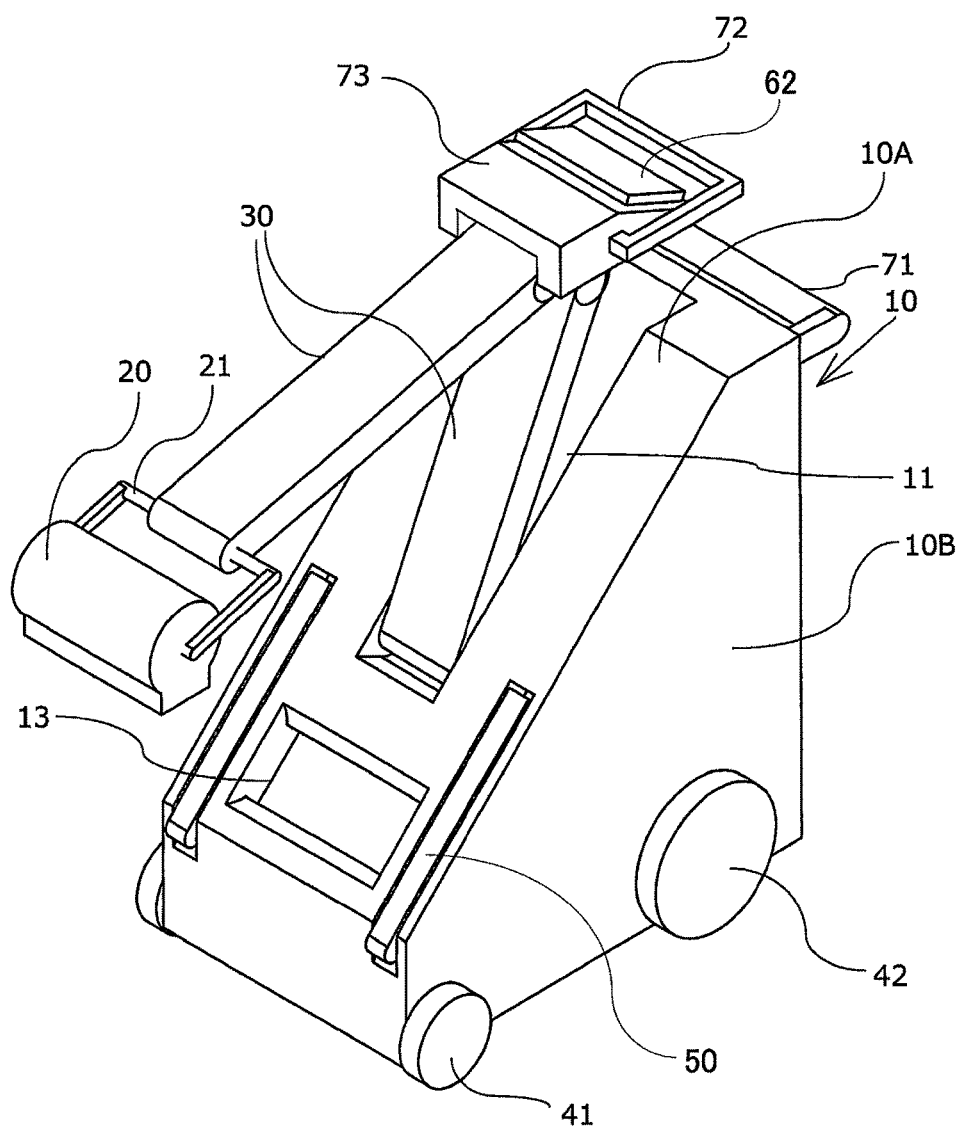
FIG. 1 is a perspective view of an X-ray imaging device viewed from the front, according to an embodiment of the invention.
Figure 2:
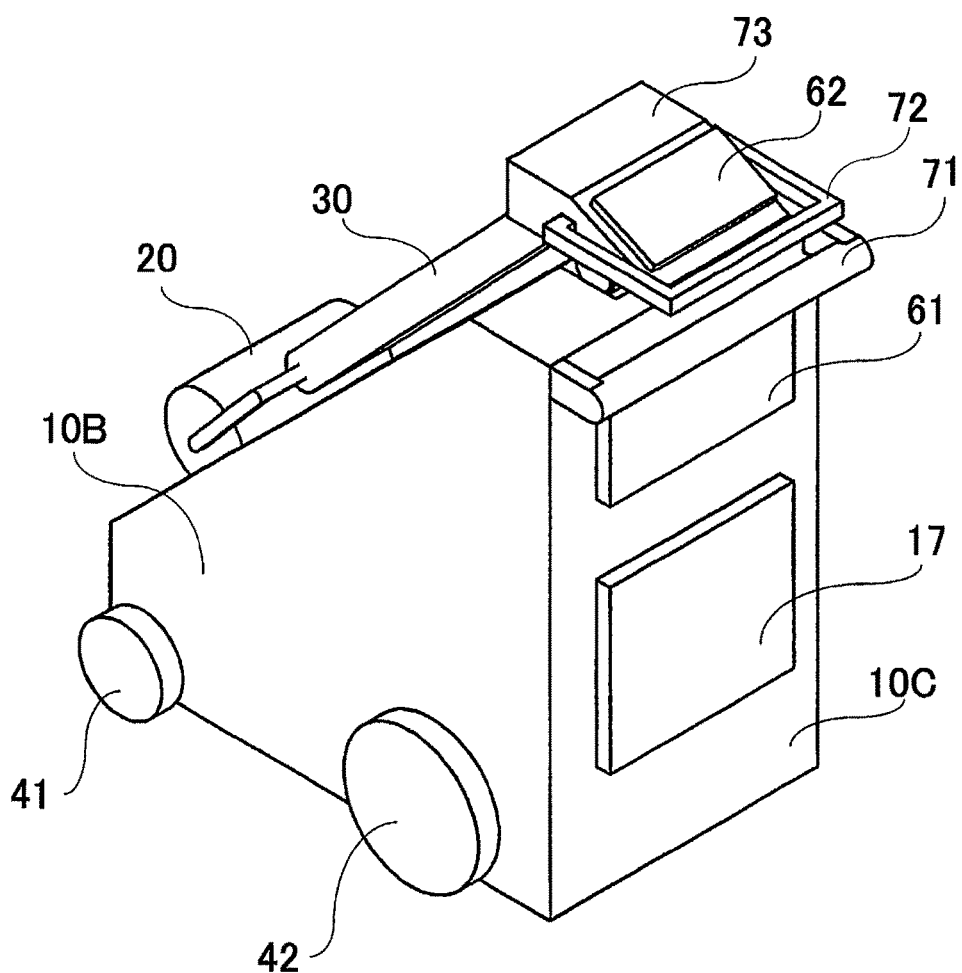
FIG. 2 is a perspective view of the X-ray imaging device viewed from the back, according to the present embodiment.
Figure 3:
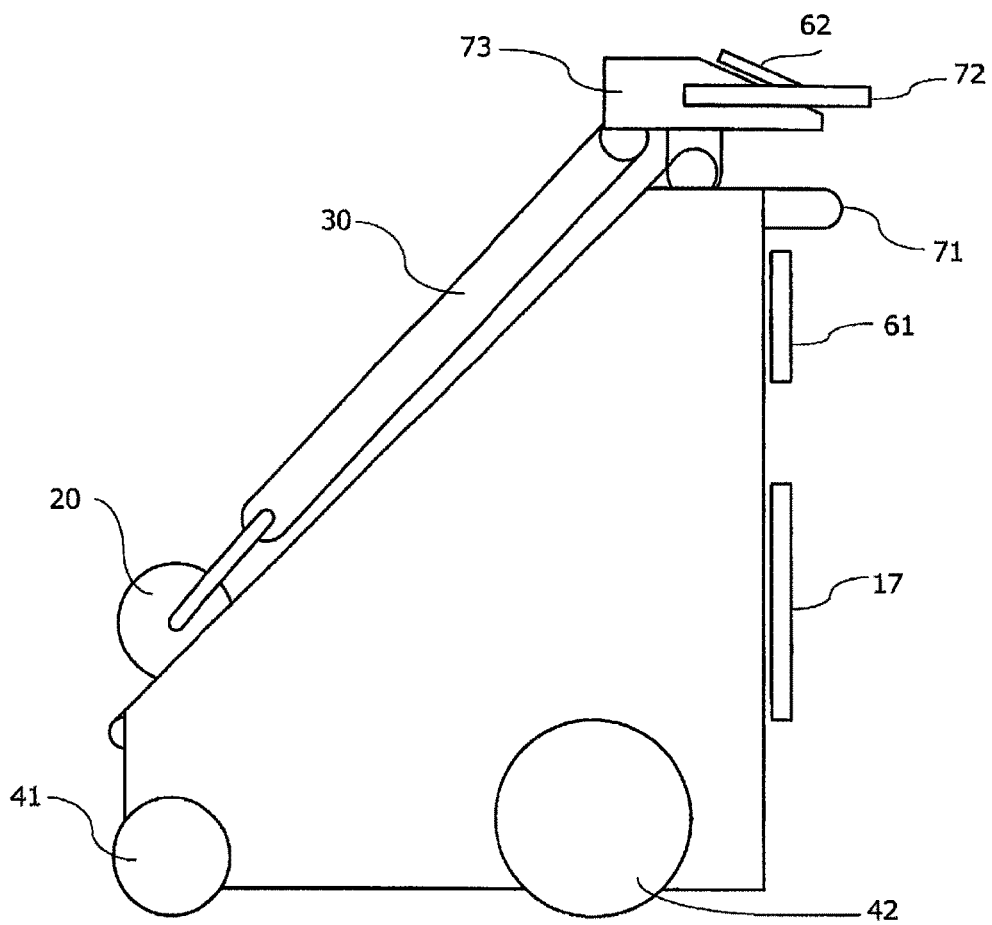
FIG. 3 is a side view of the X-ray imaging device according to the present embodiment.
Figure 4:
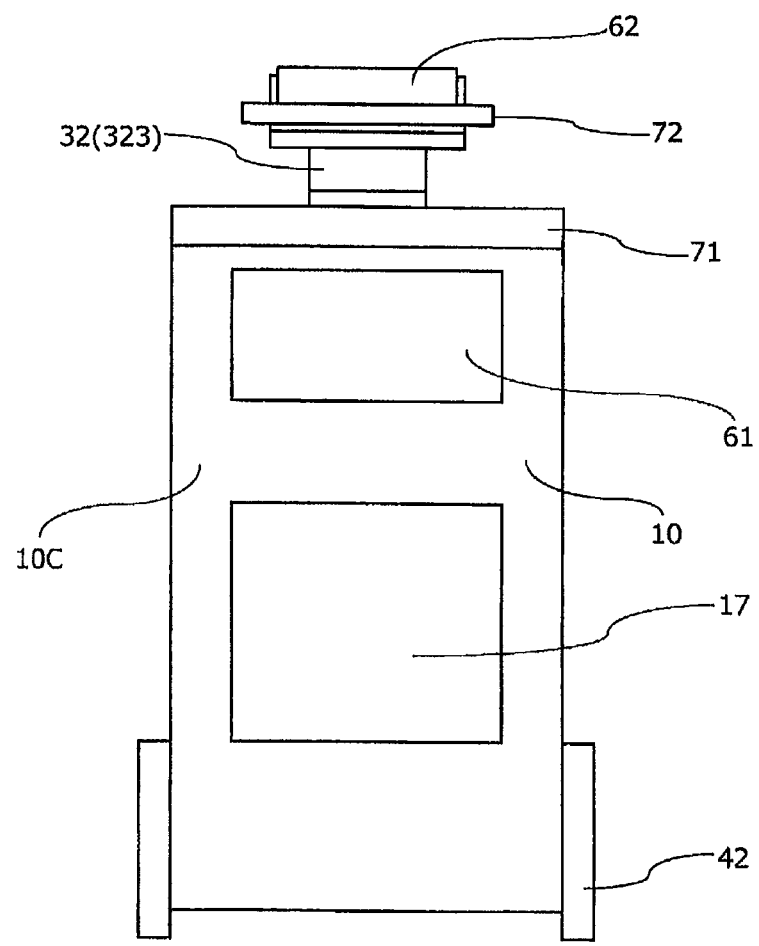
FIG. 4 is a rear view of the X-ray imaging device according to the present embodiment.

An overall structure of the mobile X-ray imaging device of the present embodiment (hereinafter, also referred to as "X-ray imaging device") will now be described with reference to FIGS. 1 to 4. FIG. 1 is a perspective view of the X-ray imaging device, viewed from the front, FIG. 2 is a perspective view of the X-ray imaging device, viewed from the back, FIG. 3 is a side view, and FIG. 4 is a rear view. It should be noted that in the present description, the front side indicates ahead of the traveling direction of the device, and the back side indicates behind the traveling direction.

As shown in FIGS. 1 and 2, the X-ray imaging device of the present embodiment comprises the main body 10 with the side surfaces of nearly triangle shape, the arm unit 30 fixed on the main body 10, the X-ray tube unit 20 fixed to one end of the arm unit 30, and the carriage (not illustrated). An enclosure constituting the main body 10 incorporates following elements, though not illustrated, such as a power supply unit for driving the carriage, a power supply unit or charging equipment for driving the X-ray tube unit 20, a control unit for driving the X-ray tube and controlling operations of mechanisms provided in the X-ray imaging device, and a balancer for controlling the center of gravity of the X-ray imaging device.

The bottom part of the main body 10 is mounted on the carriage (not illustrated) having wheels (front wheels 41 and rear wheels 42). The wheels may be mounted on the main body 10 (carriage) via a damper, a spring, or the like.

In the X-ray imaging device of the present embodiment, the front wheels 41 are casters to get the device to change direction, and the rear wheels 42 area driving wheels which are driven by the driving source, each with a diameter larger than the front wheel 41. It should be noted that the rear wheels 42 may be inclined with respect to a vertical plane, and in this case, the distance between the two rear wheels is the largest at a part coming into contact with a floor face. With this configuration, even in the case where the X-ray tube unit 20, being heavy and located forward of the rear wheels, is moved with respect to the main body 10, the main body 10 is brought into intimate contact with the floor face, thereby preventing unstable setup.

The rear wheel 42 being the driving wheel is provided with a lock such as an electronic lock for locking/unlocking the driving, allowing the device to travel only when it is unlocked.

The front panel 10A of the main body 10 is inclined or gently curved being convex outwardly, from the bottom to the top, and a storage concave 11 is provided inwardly from the panel surface for storing a part or all of the arm unit 30. The arm unit 30 is pivoted on one end within this storage concave 11, and rotating around its pivot shaft (not illustrated) allows the arm unit to move from the state being stored in the storage concave 11 to the state being pulled out as shown in FIG. 1. The storage concave 11 is further provided with a slide mechanism for allowing one end of the arm unit 30 pivoted on the storage concave 11 to move along the longitudinal direction of the storage concave 11. With this slide mechanism, the arm unit 30 moves from the position at the bottom end of the storage concave 11 to the top end position.

There is formed an X-ray tube storage 13 on the front panel 10A, continuing from the bottom end of the storage concave 11, for storing the X-ray tube unit 20 that is fixed to the arm unit 30. As shown in FIG. 3, the X-ray tube unit 20 fixed to one end of the arm unit 30 is stored in the X-ray tube storage 13, in such a manner that an X-ray radiation window (aperture) of the X-ray tube unit 20 faces to the bottom of the X-ray tube storage 13, with the arm unit 30 being stored in the storage concave 11.

A support frame 50 is mounted on the front panel 10A for supporting a portable X-ray detector (not illustrated), and grooves for storing the support frame 50 are provided on both sides of the X-ray tube storage 13 and the storage concave 11. FIG. 1 illustrates the state where the support frame 50 is stored in the grooves. The X-ray detector may be publicly known, such as an FPD (Flat Panel Detector), and imaging is performed with positioning the X-ray detector 20 so that it is opposed to the X-ray tube unit 20, placing the subject therebetween. Accordingly, the position (posture) of the X-ray detector varies in relation to the X-ray tube unit 20, and the support frame 50 serves as a base for fixing one posture of the X-ray detector.

On the other hand, as shown in FIGS. 2 and 4, the back panel 100 of the main body 10 is provided with an X-ray detector storage 17 for storing the portable X-ray detector, a display panel 61, and a transporting handle 71 for moving the X-ray imaging device.

Any structure is adaptable for use as the X-ray detector storage 17, as far as the X-ray detector can be supported stably, and any shape may be employed, such as a frame-like shape, and pocket-like shape.

The X-ray detector storage 17 may further be provided with a terminal for connecting the X-ray detector to the power supply unit and to an image forming unit, which are installed in the main body. In the case where the X-ray detector storage 17 is provided with this kind of terminal, for example, when the X-ray detector after imaging is completed is stored in the X-ray detector storage 17, the terminal of the X-ray detector is connected to the terminal of the storage 17, thereby allowing the X-ray detector to be charged, and enabling signals detected by the X-ray detector to be read by the image forming unit, so as to create and display an image. In addition, the X-ray detector storage 17 may also be provided with a source for emitting germicidal ultraviolet rays, or the like, and the source for emitting germicidal ultraviolet rays is configured to be activated when the X-ray detector is stored in the storage 17. With this configuration, the ultraviolet ray emission sterilizes the X-ray detector, every imaging time.

The display panel 61 is a unit for displaying GUI for prompting entry to the control unit and for displaying the image, and the like, as described above, and the display panel is mounted on the upper part of the X-ray detector storage 17, at a height and an angle allowing easy viewing from the operator who is standing at the back of the device. An operation panel on which operating buttons are arranged may also be mounted, together with the display panel 61.

As one example, the display panel 61 may be configured by a touch panel, and information of the subject and imaging conditions can be entered via this input screen. The information of the subject may include, for example, a patient name and a patient ID, and the imaging conditions may include a portion to be imaged, imaging date and time. Patient information may be entered by reading data from a patient ID card, or the like. The entered conditions are recorded in a recorder within the control unit that is provided in the main body 10, together with the image file being obtained, in the form of imaged data file. Details of the control unit will be described in the following.

The transporting handle 71 for moving the X-ray imaging device is fixed on the top end of the back panel 10C. The operator stands behind the back of the X-ray imaging device, and pushes the transporting handle 71, allowing the X-ray imaging device to move to a desired place. The transporting handle 71 is provided with a dead man's switch (brake-release lever), though not illustrated. When the transporting handle 71 is gripped, this brake-release lever is pushed down, releasing the lock of the carriage (rear wheels 42), and while the lever is pushed down, the carriage is allowed to travel freely. When the push-down of the lever is canceled, the rear wheels 42 are locked.

The X-ray tube unit 20 comprises an X-ray tube and equipment/mechanisms attached thereto, and in the present embodiment, the X-ray tube unit incorporates an integrated X-ray generator where a cylindrical shaped X-ray tube and a high-voltage generator are accommodated in a single case, and a movable X-ray aperture fixed on the X-ray radiation window side. In addition, an infrared distance measurer for determining a position with respect to the X-ray detector, and the like, may be attached to the movable aperture. The high voltage generator may be connected to the power supply unit accommodated in the main body 10, via a cable not illustrated. The cable is led into the main body 10 through inside the arm unit 30.

As shown in FIG. 1, the X-ray tube unit 20 is fixed to the tip of the arm unit 30 via a holder 21 that is affixed to both ends of the cylindrical-shaped cover, enabling various movements such as bi-directional rotation and swing motion, whereby the X-ray emission side (aperture unit) can be oriented to any direction.

Figure 5:
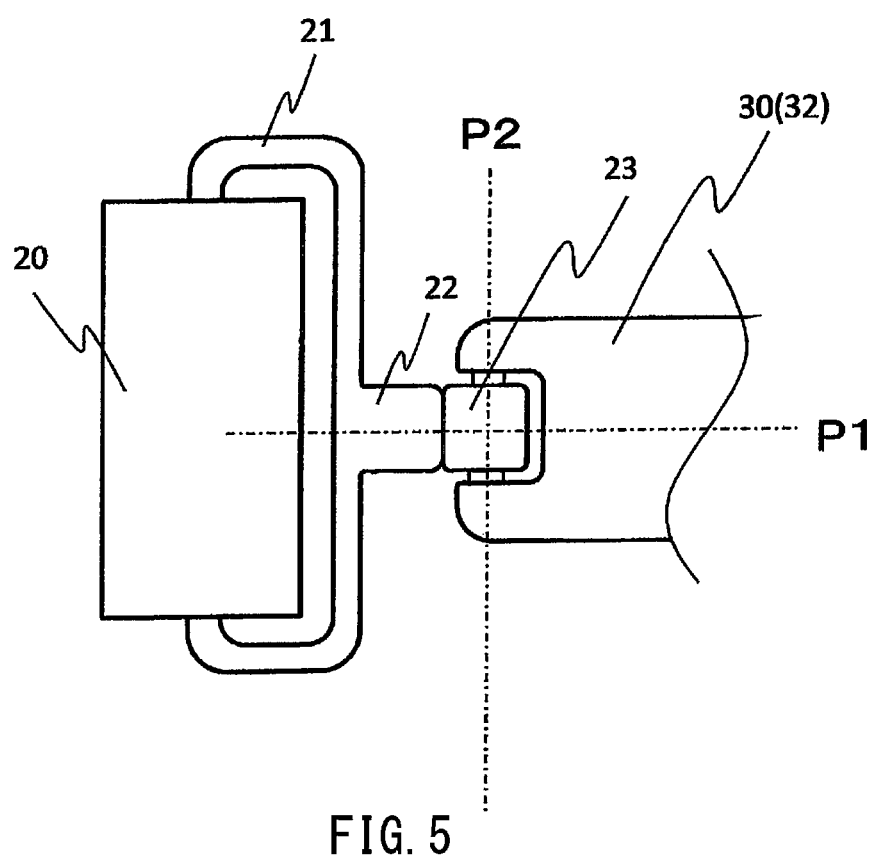
FIG. 5 illustrates a structure of the X-ray tube unit according to the present embodiment.

FIG. 5 illustrates one example of joint between the holder 21 of the X-ray tube unit 20 and the arm unit 30. In this example as shown in FIG. 5, the holder 21 has a first shaft 22 at the center thereof, and this first shaft 22 is pivoted on a second shaft 23 that is further pivoted on the tip of the arm unit 30. The first shaft 22 rotates about the axis P1 with respect to the second shaft 23, and the second shaft 23 rotates about the axis P2 orthogonal to the axis P1, with respect to the arm unit 30. With this configuration, by rotating the X-ray tube unit 20 about the axis P2, the X-ray radiation window varies its facing direction, downward, sideways (left or right), and further upward. In each of those states above, by rotating the X-ray tube unit 20 about the axis P1, the angle of the aperture unit can be changed. Further to those bidirectional rotations, it is possible to add rotation of the X-ray tube unit 20 with respect to the shaft 22, such as swing motion.

Rotations of the X-ray tube unit 20 about the axis P1 and about the axis P2 are limited to less than 360 degrees, so as to prevent wrenching the cable that is connected to the X-ray tube unit 20. A mechanical system or an electrical system may be employed as a mechanism for limiting the rotation angle. It should be noted that the joint between the holder 21 of the X-ray tube unit 20 and the arm unit 30 is not limited to the structure as shown in FIG. 5, and as shown in FIG. 1, a structure that the shaft of the holder 21 is pivoted on the arm unit 30 may also be employed.

The aforementioned rotation and swing motion of the X-ray tube unit 20 may be based on a power from a source such as a small-sized motor, and controlled by the operating unit which will be described below. The X-ray tube unit 20 may be controlled by manual operation, switched from electric operation, and in that case, a handle for manual operation (not illustrated) is mounted.

Next, with reference to FIG. 6, the arm unit and its joint part will be described.

Figure 6:
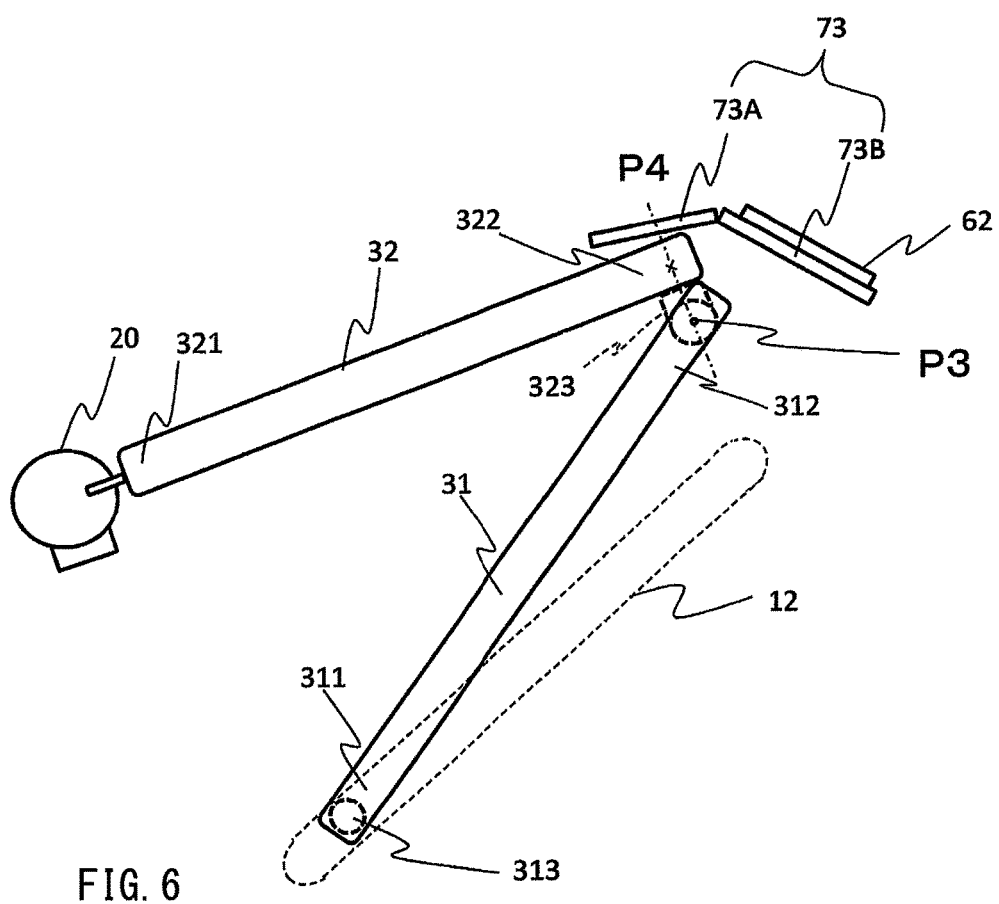
FIG. 6 illustrates a structure of an arm unit of the X-ray tube unit according to the present embodiment.

As shown in FIG. 6, the arm unit 30 in the present embodiment comprises two arms; a first arm 31 mounted on the main body 10 side and a second arm 32 to which the X-ray tube unit 20 is fixed, and the first arm 31 is foldably (rotatably) coupled to the main body 10, and the second arm 32 is coupled to the first arm 31 foldably (capable of opening and closing).

A rotation shaft of the first arm 31 is fixed on the end 311 thereof, being coupled to the main body 10, and the storage concave 11 of the main body 10 is provided with a slide mechanism for moving this rotation shaft in the longitudinal direction of the storage concave 11. A publicly known mechanism may be employed as the slide mechanism, and in the example here, long and narrow grooves (openings) may be formed in the longitudinal direction, on the bottom of the storage concave 11 or on the sides thereof, and wheels 313 are provided on both sides of the rotation shaft fixed on the end 311 of the first arm 31. With this configuration, the wheels engage with the grooves, allowing a slide in the grooves. Any other combination may be applicable, in addition to the combination of groove and wheel, such as a combination of rail and wheel, and a combination of rack and pinion. Accordingly, the end 311 of the first arm 31 is allowed to move from the bottom end of the storage concave to the top end thereof.

The dotted line in FIG. 6 indicates, as the slide mechanism, the long and narrow openings 12 which are provided on the sides of the storage concave 11. The wheels 313 provided on the end of the first arm 31, engaging with the openings 12, are mounted on the shaft passing through the end 311 in the direction orthogonal to the longitudinal direction of the first arm 31. This configuration allows the first arm 31 to rotate about the shaft of the wheels, thereby varying the angle with respect to the front panel 10A.

The second arm 32 is fixed to the end 312 of the first arm 31, capable of opening and closing, as well as rotating, the end 312 being on the opposite side of the end 311 fixed on the main body 10. As shown in FIG. 6, for instance, the end 322 of the second arm 32 is coupled to the end 312 of the first arm 31, via the shaft 323. The shaft 323 is pivoted on the axis P3 at the end 312 of the first arm 31, allowing rotation about the axis P3. The end 322 of the second arm 32 is pivoted on the axis P4 with respect to the shaft 323, allowing rotation (swiveling) around the axis P4.

It should be noted that the mechanism as shown in FIG. 6 is an example for achieving the foregoing movement of the second arm 32 with respect to the first arm 31. On the contrary, it may be configured such that the shaft 323 rotates about the axis P4 with respect to the first arm, and the second arm 32 rotates about the axis P3 with respect to the shaft 323. Further alternatively, another joint mechanism may be employed.

The aforementioned sliding and rotation (variation of the opening angle) of the first arm, and the rotation (variation of the opening angle and the swiveling angle) about the axes P3 and P4 of the second arm, may be performed manually by using the arm operating handle described in the following. Alternatively, an electrical drive source such as a motor (not illustrated) may be utilized subsidiarily. The driving source may facilitate moving of the arm unit 30 on which the weighty X-ray tube unit 20 is mounted, with the use of the handle or operation equipment, and further, operation of the arm unit 30 may be semi-automated.

The arm unit 30 is further provided with a mechanism (not illustrated) for locking and unlocking the first and second arms 31 and 32 at a predetermined slide position or rotational position, in association with the slide mechanism and the rotation mechanism of the first arm 31, and the rotation mechanism of the second arm 32. The lock mechanism functions as locking the sliding and rotation of the first and second arms 31 and 32, mechanically or electrically, and an electric lock may be employed, for instance. Locking and unlocking can be performed by operating a pedal, lever, or button.

Preferably, the arm unit 30 may be further provided with a position detector such as encoder, for detecting a position in the slide direction, the opening angle, and swiveling angle of the first and second arms 31 and 32. When the arm unit 30 is moved by using the drive source, detected results of the positions and angles of the first and second arms 31 and 32, obtained by the position detector may be utilized for controlling the arm unit 30.

Next, a joint between the first arm 31 and the second arm 32 (also referred to as a joint of the arm unit) will be described.

As shown in FIGS. 1 and 3, a cover 73 is mounted on the joint between the arm units. The cover 73 is fixed on (pivoted on) the end 322 of the second arm 32, and the ends of an arm operating handle 72 (hereinafter, it is also simply referred to as a handle 72) for operating the arm unit 30 are integrally fixed to the sides of the cover 73. The shape of the cover 73 is not particularly limited, but in the embodiment as illustrated, two top panels 73A and 73B (FIG. 6) are coupled to each other at an obtuse angle, having a shape of a plate joining slim side-panels to both sides of the plate. In FIG. 6, the side-panels are not shown, and only the top panels 73A and 73B are schematically illustrated.

Even when the first arm 31 rotates, the cover 73 allows the upper plate 73A to keep a nearly horizontal position.

Out of the top panels 73A and 73B constituting the cover 73, on the top panel 73B that is positioned on the rear side, there is provided a tablet fixing part for attaching a tablet-type operating/display unit 62 (hereinafter, referred to as an operating tablet), and the operating tablet 62 is attached to the tablet fixing part. As described above, since the cover 73 is made up of the top panels 73A and 73B being joined at an angle, a tilt angle of the operating tablet 62 is given with respect to the horizontal plane, facilitating viewing of the screen by the operator. The operating tablet 62 may be mounted on the cover 73 or may be detachable from and attachable to the cover 73. In the present embodiment, a configuration being detachable and attachable will be described.

The operating tablet 62 is, for example, an LCD unit with a touch panel, and it may be provided with a display function which is different from the display panel 61 fixed on the back side of the main body 10, or it may be provided with a display function that supplements the display panel 61. By way of example, the operating tablet 62 may be dedicated to GUI for operation, or a display panel for displaying an image, or it may be a display used for both purposes. As one example of the operation, via the UI displayed on the display screen, information necessary for the device may be entered, or a command necessary for drive-control of the arm unit 30 and the X-ray tube unit 20 may be entered. The information and command entered from the operating tablet 62 are transferred to the control unit of the main body 10, and the control unit controls operations of the mechanisms for driving the arm unit 30 and the X-ray tube unit 20.

Driving of the arm unit 30 and the X-ray tube unit 20 may include, for example, adjustments from an initial position to an imaging position, i.e., moving the arm unit 30 stored in the storage 11 to the initial position being predetermined and positioning the X-ray tube unit to the initial position; and further include rotation, swiveling, and swing of the X-ray tube unit 20 with respect to the arm unit 30. The initial position is not particularly limited, but this position allows movement within a range keeping the arm unit and the X-ray tube unit from contact with other objects or human being, even though the arm unit and the X-ray tube unit are automatically moved. By way of example, the initial position is a position where the angle of the first arm 31 is increased with respect to the main body 10 while sliding within the storage 11, and the angle of the second arm 32 with respect to the first arm 31 is increased, in such a manner that the X-ray tube unit 20 does not protrude outwardly from the main body 10.

Accordingly, there are provided on the tablet fixing part of the top panel 73B, terminals for connecting the operating tablet 62 with the control unit and the power supply unit accommodated within the main body 10. Similarly, there are provided on the operating tablet 62 side, terminals to be connected to the terminals on the main body, and when the operating tablet 62 is attached to the tablet fixing part, those terminals are connected respectively, as well as secured mechanically. The terminal may have any publicly known configuration, including a USB terminal. One of those terminals may be a terminal for establishing connection with the power supply unit. In this case, by attaching the operating tablet 62 on the tablet fixing part, the operating tablet 62 is connected to the power supply unit on the main body side, whereby the operating tablet is driven by the power delivered from the power supply unit, and a rechargeable battery built in the operating tablet 62 is charged.

In the case where a function for wireless communication between the operating tablet 62 and the main body 10 is provided, the connection via the terminals is not required, and the fixing part may only have a frame structure or a concave structure, allowing the input display unit 62 to be held stably.

The handle 72 used by the operator for operating the arm unit 30 may be mounted on the cover 73.

Figure 7:
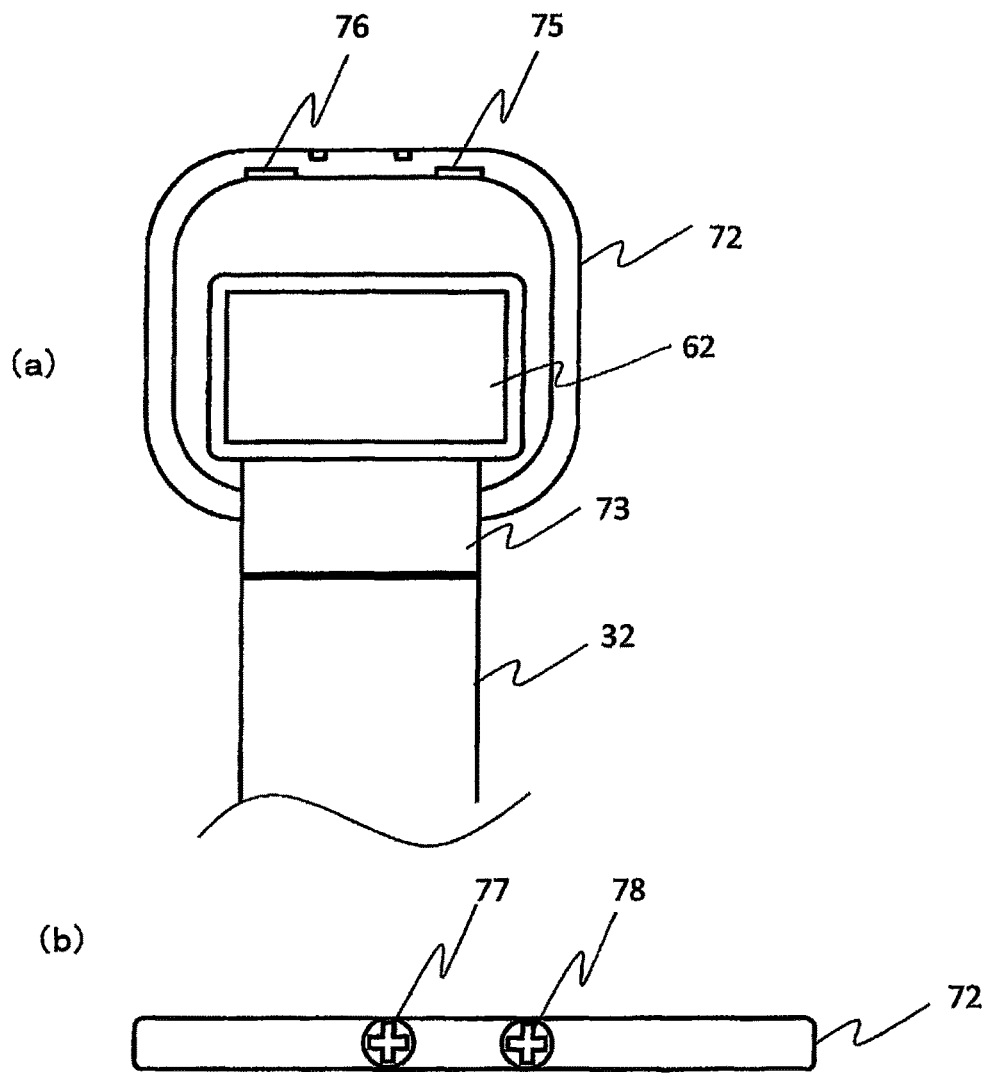
FIG. 7 illustrates a handle of a mobile X-ray imaging device according to the present embodiment.

As shown in FIG. 7(*a*), in the present embodiment, the handle 72 is provided with the dead man's switches 75 and 76, which keep movement while those switches are pressed down. Press-down of the switches 75 and 76 according to an action of grasping the handle 72 may release the lock mechanism, e.g., an electromagnetic lock for locking the positions of the first arm and the second arm, thereby enabling movement of the arms. As for the slide position, the lock may be released only when both the switches 75 and 76 are pressed down, for instance. Alternatively, a switch for locking/unlocking the slide position may be provided, in addition to the switches 75 and 76.

With this configuration, by lifting up the handle 72, for instance, the end 312 of the first arm 31 is raised, thereby varying the angle (opening angle) with respect to the main body 10. By raising the handle 72 backwardly and upwardly from the device, the end 311 of the first arm 31 is made to slide to move toward an upper part of the storage concave 11. This sliding toward the upper part of the first arm 31 may be associated with the opening angle. In this case, along with upward sliding of the first arm 31, the opening angle is made larger, configuring such that the first arm 31 becomes nearly upright when the first arm 31 is moved to the top end of the storage concave 11.

After raising the first arm 31 up to a predetermined slide position, the slide mechanism is locked, and then the opening angle between the first arm 31 and the second arm 32 is adjusted.

If the switches 75 and 76 are not operated, both the first arm 31 and the second arm 32 are locked and immovable. However, if the switch 76 is pressed down, for example, while the handle 72 is being grasped, the lock of the first arm 32 is released. In this situation, when the operator presses down or presses up the handle 72, the second arm 32 rotates about the axis P3, resulting in that the end 321 to which the X-ray tube unit 20 is fixed goes up or down, thereby varying the position of the X-ray tube unit 20. By suspending the press-down operation of the switch 76, the second arm 32 is retained at the position.

Turning the handle 72 left and right, in the state that rotation of the first arm 31 and the second arm 32 in the opening-angle direction is locked, enables the second arm 32 to revolve, i.e., to swivel around the axis P4. Accordingly, the X-ray tube unit 20 is allowed to swivel laterally.

Manipulation of the arm unit 30 by the handle 72 as described above is just an example, and it does not restrict the present embodiment. In the case where the sliding and rotation of the first arm 31, and the rotation of the second arm are performed by electrical driving units, the aforementioned lifting operation, raising operation, or turning operation according to the operating handle 72 may trigger transmission of control signals to activate the driving unit.

As shown in FIG. 7(*b*), the handle 72 may be provided with operation buttons 77 and 78 for rotating the X-ray tube unit 20. In the illustrated example, the operation buttons 77 and 78 are provided for the rotation of the X-ray tube unit 20 as shown in FIG. 5, respectively about the axis P1 and about the axis P2, and those buttons are provided on the positions facilitating manipulation by the thumb of a hand grasping the handle 72, for example, on the outside surface of the handle 72. With this configuration, the X-ray tube unit 20 can be manipulated to rotate and swing, even from a location away from the X-ray tube unit 20, so as to set the X-ray tube unit 20 at a position facing the X-ray detector.

Figure 8:
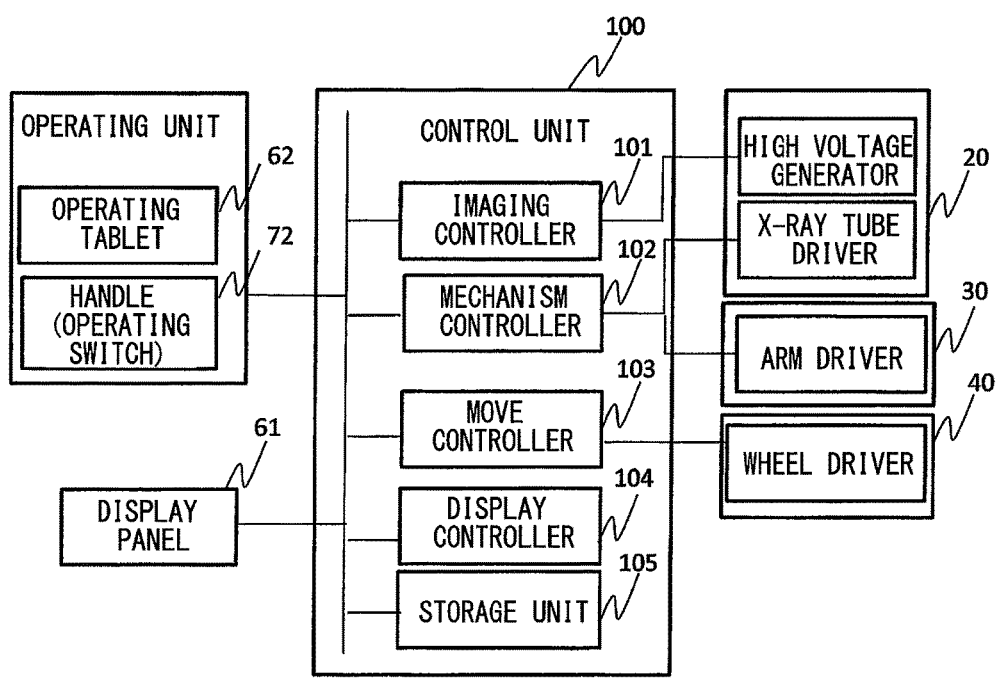
FIG. 8 is a functional block diagram of a control unit of the X-ray imaging device according to the present embodiment.

Next, with reference to FIG. 8, the control unit provided in the main body 10 will be described. As shown in FIG. 8, the control unit 100 incorporates an imaging controller 101 that controls the X-ray driving unit to start and stop imaging, a move controller 103 that controls driving of the carriage (rear wheel 42) of the X-ray imaging device, a mechanism controller 102 that controls mechanical elements for moving the arm unit 30 and the X-ray tube unit 20, a display controller 104 that controls images displayed on the display panel 61 and the input display unit 62, and a storage unit 105 for storing information, data, and the like, necessary for the control.

The display panel 61 and the operating tablet 62 function as input units, together with other operating switches (e.g., a power ON/OFF switch, and operation buttons 77 and 78 as shown in FIG. 7(*b*)), and the commands and information entered from those elements are transferred to the control unit 100. It is principally configured such that a command to the move controller 103 is entered via the display panel 61, whereas a command to the mechanism controller 102 is entered via the operating tablet 62.

The screen of the display panel 61 comprises an area where the operation buttons are displayed, an area for displaying an image, and an area for displaying the subject information. Under the control of the display controller 104, those areas can be made larger or smaller, and overlaid one on another.

Under the control of the display controller 104, the operating tablet 62 may have a configuration to perform switching, for example, switching the display mode between a display mode for delivering commands to the mechanism controller 102 (mechanical operation mode), and a mode for displaying the same screen as the display panel 61 (basic mode).

Figure 9:
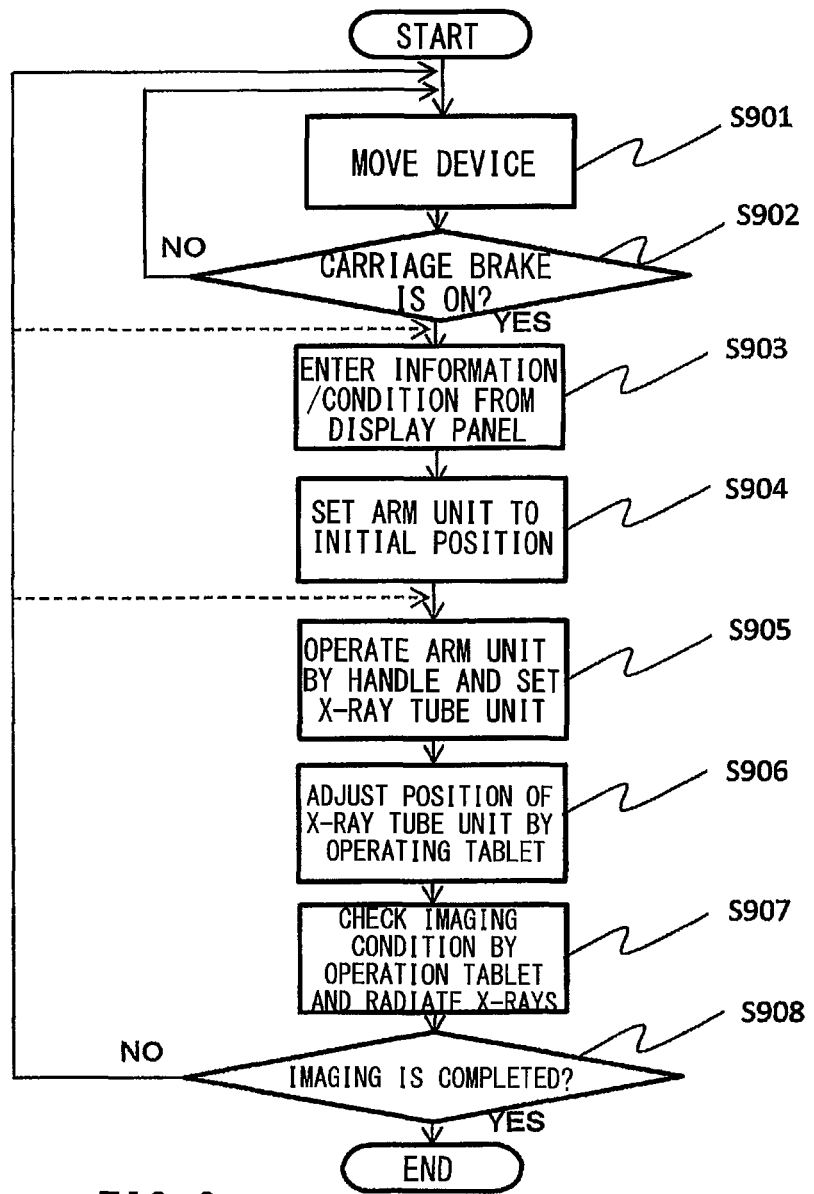
FIG. 9 illustrates one example of an operational procedure of the X-ray imaging device.

With reference to FIG. 9, one example of the imaging procedure according to the foregoing configuration will be described. Firstly, in the state the console starts up by turning on the power, the brake is released by grasping the brake release lever on the transporting handle 71, and the device is moved to a predetermined location by manipulating the handle 71 (S901). Brakes are applied to the carriage (rear wheels 42), and after ensuring that the device stops traveling at a location where the imaging is performed (S902), the imaging works are prepared. At first, subject information is entered from the display panel 61, together with the imaging conditions (S903).

Figure 10:
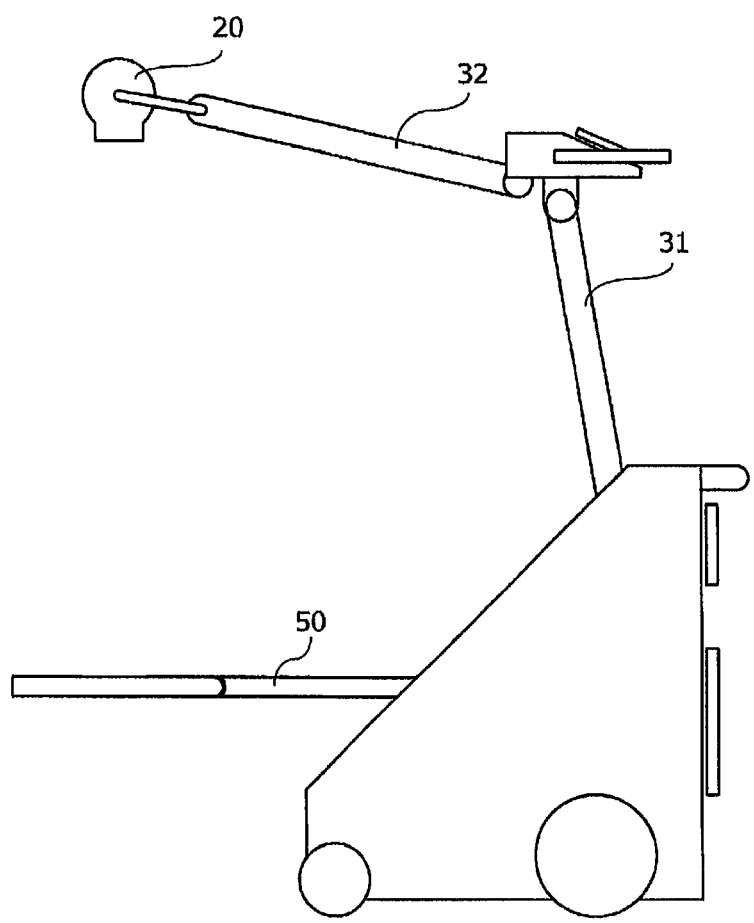
FIG. 10 is a side view showing one example of the X-ray imaging device posture.

Next, the operating tablet 62 is operated to set the arm unit 30 and the X-ray tube unit 20 at initial positions (S904). Alternatively, the arm operating handle 72 is operated manually. By way of example, the angle which the first arm 31 forms with the main body 10 is changed along with lifting up the first arm 31, and it is made nearly upright as shown in FIG. 10. Furthermore, if necessary, together with varying the position of the first arm 31, the second arm 32 is turned with respect to the first arm 31, so as to set the X-ray tube unit 20 at a predetermined height (S905).

Figure 11:
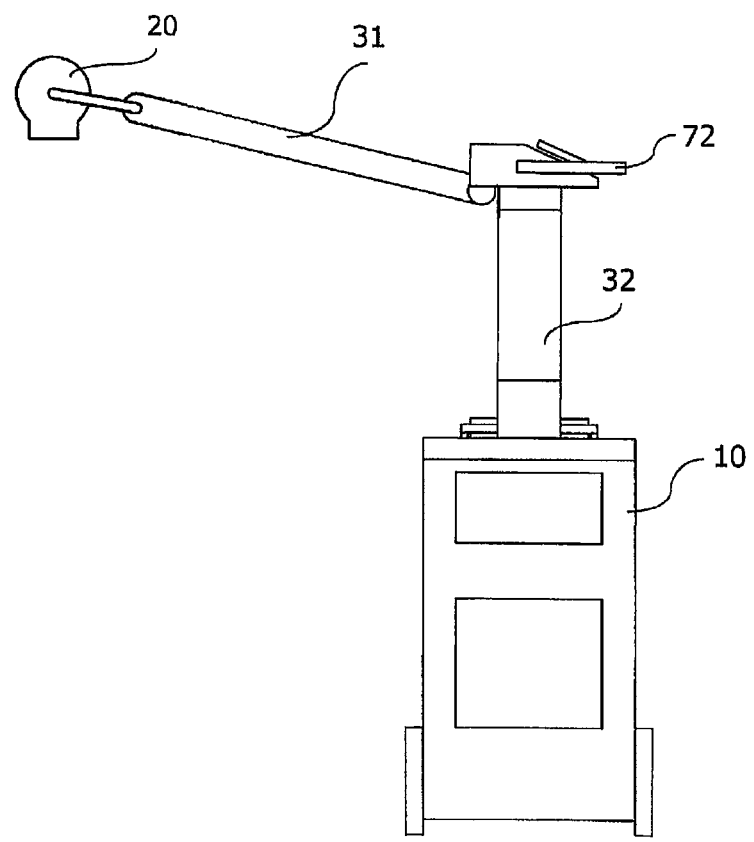
FIG. 11 is a rear view showing another example of the X-ray imaging device posture.

If swiveling of the second arm 32 is not necessary, as shown in FIG. 10, the support frame 50 of the X-ray detector is pulled out of the front panel 10A of the main body 10, putting the X-ray detector on the support frame 50, and then the subject is placed between the X-ray detector and the X-ray tube unit 20. If the condition of the subject requires to swivel the second arm 32, the X-ray detector is placed under the subject, and the arm operating handle 72 is operated to swivel the second arm 32 as shown in FIG. 11, so that the second arm is positioned just above the subject. In this case, it is further possible to set the operating tablet 62 as the mechanical operation mode, and to control driving of the arm via the operating tablet 62.

After setting the X-ray tube unit 20 at a predetermined position by moving the arm unit 30, rotating/swiveling or swing motion of the X-ray tube unit 20 may be performed with respect to the arm unit, thereby determining the position of the X-ray tube unit (S906). Driving of the X-ray tube unit 20 is controlled via the switches 77 and 78 provided on the handle 72, or via the operating tablet 62. In controlling the driving of the X-ray tube unit 20, it is possible to determine in advance which receives a highest priority, the switches 77 and 78 of the handle 72 or the operating tablet 62. Alternatively, the priorities may be changed by switching the mode of the operating tablet 62. For example, when the operating tablet 62 is in the mechanical operation mode, a priority is assigned to a command from the operating tablet 62.

A location of the operator upon manipulating the arm unit 30 and the X-ray tube unit 20 via the handle 72 is not necessarily the position that faces to the display panel 61 provided on the main body 10. However, since the operator faces the handle 72 and the operating tablet 62, the aforementioned operations can be performed easily.

Thereafter, the display mode of the operating tablet 62 is changed to the basic mode, and after checking the information entered from the display panel 61, information may be added or modified as required, and imaging is started on the spot (S907). If another imaging is performed in succession (S908), the carriage is moved as necessary, and the aforementioned steps from S901 to S906 are iterated. If the carriage is not moved, the procedure returns to the step S903 or the step S905, and the steps up to S907 are repeated.

According to the present embodiment, a joint between two arms is provided with the operating unit for operating the X-ray tube unit coupled to the tip of the arm, whereby the operator is allowed to easily operate the X-ray tube unit at a position that facilitates the operation by the operator, even when the position of the X-ray tube unit is high or low.

In addition, the operating unit also serves as the display unit, whereby the operator is allowed to easily confirm the information such as the subject information and the imaging conditions that are to be checked upon imaging.

In addition, provision of the arm operating handle for operating the X-ray tube unit enables operation with perceiving through intuition the movement of the X-ray tube unit. The arm operating handle is further provided with switches for operating the motions of the X-ray tube unit, such as rotation and swiveling with respect to the arm unit, thereby enhancing the operability.

Modification Example

In the foregoing embodiment, there has been described the X-ray imaging device having the joint of the arm unit, provided with both the operating/display unit and the arm operating handle. The present invention includes, however, a configuration where only either one of the operating/display unit and the arm operating handle. In other words, the X-ray imaging device as shown in FIG. 1 and some other figures, is described as having the joint of the arm unit 30 that is provided with both the handle 72 and the operating/display unit 62. There is a modification example of the X-ray imaging device where the operating/display unit 62 is not provided but the handle 72 is provided, or another modification example of the X-ray imaging device where the handle 72 is not provided, but the operating/display unit 62 is provided. There is another example of the X-ray imaging device provided with the arm operating handle 72, and the handle 72 is not provided with any operating switch for operating the X-ray tube unit 20.

It has been described that in the aforementioned embodiment, the arm unit comprises two arms, but the number of arms constituting the arm unit is not limited to two. By way of example, three arms may constitute the arm unit, or one or two arms may be configured by linkage.

In addition, among various elements described in the aforementioned embodiments, the elements except the operating/display unit and the arm operating handle may be omitted as appropriate. By way of example in the first embodiment, there has been described the X-ray imaging device that is provided with the storage on the front surface of the main body, for storing the arm unit. The present invention may be applied, for instance, to a device where the arm unit is connected directly to the main body or to another structure different from the main body as described in the Patent Document 1. One example where the arm slides with respect to the main body has been described. It is further possible that the arm swivels only, without changing the position of the arm.

INDUSTRIAL APPLICABILITY

According to the present invention, the X-ray imaging device with improved operability is provided, adaptable to the X-ray imaging device for use in patient visit.

DESCRIPTION OF SYMBOLS

10 . . . main body, 20 . . . X-ray tube unit, 30 . . . arm unit, 31 . . . first arm, 32 . . . second arm, 50 . . . support frame for X-ray detector, 61 . . . display panel (display unit on the main body side), 62 . . . operating/display unit (operating tablet), 71 . . . transporting handle, 72 . . . arm operating handle

What is claimed is:
1. An X-ray imaging device, comprising:
an X-ray tube unit,
a main body provided with a drive unit of the X-ray tube unit, and
an arm unit configured to connect the X-ray tube unit with the main body, the X-ray tube unit being fixed to one end of the arm unit, and the arm unit comprises plural foldable arms, an operating unit configured to manipulate the X-ray tube unit is provided on a joint between two of the arms, and
a cover that covers the joint between the two of the arms, wherein the operating unit is attached to the cover.

2. The X-ray imaging device according to claim 1, wherein,
the operating unit is a display unit serving as both the operating unit and the display unit.

3. The X-ray imaging device according to claim 2, wherein,
the operating unit is detachable from and attachable to the cover.

4. The X-ray imaging device according to claim 2, wherein,
the main body comprises a control unit, and
the control unit further comprises a display controller configured to control the operating unit, and
the operating unit is a display unit serving as both the operating unit and the display unit.

5. The X-ray imaging device according to claim 1, wherein,
a handle configured to manipulate the arms is attached to the cover.

6. The X-ray imaging device according to claim 1, wherein,
the main body is fixed on a carriage, thereby rendering the device to be movable.

7. An X-ray imaging device comprising:
an X-ray tube unit,
a main body provided with a drive unit of the X-ray tube unit, and
an arm unit configured to connect the X-ray tube unit with the main body, the X-ray tube unit being fixed to one end of the arm unit, and the arm unit comprises a first arm coupled to the main body, and a second arm having the X-ray tube unit fixed on the end thereof, and
an operating unit configured to manipulate the X-ray tube unit is provided on a joint between the first arm and the second arm,
the first arm is coupled to the main body in a slidable manner as well as rotatable in opening and closing directions, the second arm is coupled to the first arm, in a manner rotatable in opening and closing directions and swivels around an axis in a longitudinal direction of the first arm, and
a handle configured to manipulate sliding and rotation of the first arm, and rotation and swiveling of the second arm is attached to the joint.

8. The X-ray imaging device according to claim 7, wherein,
the handle comprises an operating switch configured to control movement of the X-ray tube unit.

9. The X-ray imaging device according to claim 8, wherein,
the X-ray tube unit is coupled to one end of the arm unit in such a manner that at least one operation of: rotation, swiveling, and swing motion is performed, and the operating switch controls the at least one operation.

10. The X-ray imaging device according to claim 7, wherein,
the operating unit is a display unit serving as both the operating unit and the display unit.

11. The X-ray imaging device according to claim 7, further comprising a cover that covers the joint between the arms, wherein,
the operating unit is attached to the cover.

12. The X-ray imaging device according to claim 11, wherein,
the operating unit is detachable from and attachable to the cover.

13. The X-ray imaging device according to claim 7, wherein,
the main body comprises a control unit, and
the control unit further comprises a display controller configured to control the operating unit, and
the operating unit is a display unit serving as both the operating unit and the display unit.

14. The X-ray imaging device according to claim 7, wherein,
the main body is fixed on a carriage, thereby rendering the device to be movable.

15. An X-ray imaging device, comprising:
an X-ray tube unit,
a main body provided with a drive unit of the X-ray tube unit, and
an arm unit configured to connect the X-ray tube unit with the main body, the X-ray tube unit being fixed to one end of the arm unit, and the arm unit comprises plural foldable arms,
an operating unit configured to manipulate the X-ray tube unit is provided on a joint between two of the arms, and
a handle for manipulating the arms is provided on a joint between two of the arms,
wherein the operating unit is also a display unit.

* * * * *